(12) United States Patent
Barbul et al.

(10) Patent No.: US 12,117,349 B2
(45) Date of Patent: Oct. 15, 2024

(54) SENSOR SYSTEM, SENSOR ARRAY AND PROCESS OF USING THE SENSOR SYSTEM

(71) Applicant: TDK Corporation, Tokyo (JP)

(72) Inventors: Andreas Barbul, Munich (DE); Matthias König, Munich (DE)

(73) Assignee: TDK Corporation, Tokyo (JP)

( * ) Notice: Subject to any disclaimer, the term of this patent is extended or adjusted under 35 U.S.C. 154(b) by 302 days.

(21) Appl. No.: 17/706,918

(22) Filed: Mar. 29, 2022

(65) Prior Publication Data

US 2022/0316958 A1    Oct. 6, 2022

(30) Foreign Application Priority Data

Mar. 30, 2021 (DE) ........................ 102021108090.8

(51) Int. Cl.
*G01K 1/16*    (2006.01)

(52) U.S. Cl.
CPC ..................... *G01K 1/16* (2013.01)

(58) Field of Classification Search
CPC    G01K 7/25; G01K 1/16; G01N 27/16; G01N 25/32; G01N 33/004
USPC ...................................................... 374/165
See application file for complete search history.

(56) References Cited

U.S. PATENT DOCUMENTS

| | | | | |
|---|---|---|---|---|
| 5,048,336 A * | 9/1991 | Sugihara | ........... | G01N 27/18 338/35 |
| 5,551,283 A * | 9/1996 | Manaka | ........... | G01F 1/69 73/75 |
| 6,508,585 B2 * | 1/2003 | Nakamura | ........... | A61P 9/00 374/10 |
| 2003/0056570 A1 * | 3/2003 | Shin | ........... | G01N 25/32 73/25.05 |
| 2004/0026268 A1 * | 2/2004 | Maki | ........... | G01N 27/407 204/426 |
| 2010/0242592 A1 * | 9/2010 | Haneef | ........... | G01N 3/24 73/204.26 |
| 2011/0048127 A1 * | 3/2011 | Matsumoto | ........... | G01N 27/18 73/204.26 |
| 2016/0077032 A1 * | 3/2016 | Hattori | ........... | G01N 33/0027 422/95 |
| 2016/0103082 A1 * | 4/2016 | Kimura | ........... | G01N 33/005 73/25.01 |
| 2018/0328872 A1 * | 11/2018 | Nakano | ........... | G01N 27/18 |
| 2019/0035607 A1 | 1/2019 | Kim et al. | | |
| 2019/0128827 A1 * | 5/2019 | Bao | ........... | G01N 25/482 |
| 2019/0311824 A1 * | 10/2019 | Kohl | ........... | G05D 23/2401 |
| 2019/0339196 A1 * | 11/2019 | Abel | ........... | G01N 33/004 |
| 2019/0353607 A1 * | 11/2019 | Kaita | ........... | G01N 27/028 |
| 2020/0080951 A1 * | 3/2020 | Nakano | ........... | G01N 27/18 |
| 2021/0003525 A1 * | 1/2021 | Kaita | ........... | G01N 33/006 |
| 2021/0132014 A1 * | 5/2021 | Goel | ........... | G01N 33/004 |
| 2021/0293735 A1 * | 9/2021 | Matsuo | ........... | G01N 27/18 |

(Continued)

*Primary Examiner* — David J Bolduc
(74) *Attorney, Agent, or Firm* — Slater Matsil, LLP

(57) ABSTRACT

In an embodiment a sensor system includes a first sensor having a first thermistor configured to sense a change in heat flow and a first heater configured to heat the first thermistor and a second sensor having a second thermistor configured to sense a change in heat flow and a second heater configured to heat the second thermistor, wherein a heat conduction path between the first heater and the first thermistor has a higher thermal conductivity than a heat conduction path between the second heater and the second thermistor.

20 Claims, 2 Drawing Sheets

(56) References Cited

U.S. PATENT DOCUMENTS

2022/0299461 A1\* 9/2022 Barbul .................. G01N 27/16
2023/0101259 A1\* 3/2023 Kasai ..................... G01F 1/696
                                                    73/204.23

\* cited by examiner

SENSOR SYSTEM, SENSOR ARRAY AND PROCESS OF USING THE SENSOR SYSTEM

CROSS-REFERENCE TO RELATED APPLICATIONS

This application claims the priority of German Application No. 102021108090.8, filed on Mar. 30, 2021, which application is hereby incorporated herein by reference.

TECHNICAL FIELD

The present application relates to a sensor system, a sensor array comprising the sensor system and a process of using the sensor system.

BACKGROUND

Sensing of individual gas concentrations in gas mixtures is required for many technical applications, including exhaust control or control of a working environment and similar applications.

US Patent Application Publication No. 2019/35607 A1 describes gas sensor setups relying on measuring the gas concentration via changes in the thermal conductivity of the atmosphere by a thermistor or via a reaction heat created by a reaction of a reactive gas on a catalyst.

SUMMARY

Embodiments provide sensors with improved sensitivity. Further embodiments provide sensors with improved response time while maintaining a certain sensitivity.

According to a first embodiment a sensor system is provided. The sensor system comprises two sensors, i.e. a first sensor and a second sensor. The first sensor has a first thermistor for sensing a change in heat flow and a first means for heating the first thermistor. Similarly, the second sensor has a second thermistor for sensing a change in heat flow and a second means for heating the second thermistor. In this setup the heat conduction path between the first means for heating and the first thermistor has a higher thermal conductivity than the heat conduction path between the second means for heating and the second thermistor.

In this setup, the means for heating may be any means capable of heating the respective thermistor. For example, the means for heating may be means for resistive heating, such as a heating meander which has a meander-like form and which may be provided on a substrate. Such a substrate may be a common substrate for both sensors, but may also be two separate substrates within the sensor system.

In the above sensor system, the heat conduction path for the first thermistor, which is the path along which the heat is conducted between the first means for heating and the first thermistor, has a higher thermal conductivity than the heat conduction path for the second thermistor. This configuration has the advantage that the response on both sensors to a change in the surrounding atmosphere is different. Such a change may be a change in the gas composition of the atmosphere. This may alter the heat flow from the thermistor to the atmosphere, which affects the temperature of the thermistor. For example, the inventors have found that the temperature change of the first thermistor induced by a change in gas composition is smaller than that of the second thermistor. The inventors assume that the higher thermal conductivity enables a more direct thermal coupling of the first thermistor to the first means for heating than for the second thermistor to the second means for heating. As is shown below, this effect can be applied preferentially if the first and the second sensor are operated at different temperatures, and in particular in the case the second sensor is operated at higher temperature than a first sensor.

This may increase sensitivity of the sensor system. Furthermore, an advantage over state of the art sensors may be provided in which the heat conduction path for a first and a second sensor is typically the same or basically the same.

Generally, this principle may be applied to the detection of any gas which affects the heat transport from a thermistor. This may occur for inert gases by a change in thermal conductivity upon a change in gas composition. For a reactive gas, a difference in heat transport from or to the thermistors may be induced by a chemical reaction on a catalyst on the thermistor. The thermistor may, for example, be applied to the detection of $CO_2$ as an inert detectant. Examples for reactive gases may be CO or carbon hydrates.

According to an embodiment, the heat conduction path between the first means for heating and the first thermistor includes the first thermistor itself. Similarly, the heat conduction path between the second means for heating and the second thermistor includes the second thermistor itself. In this case, the first thermistor has a higher thermal conductivity than the second thermistor. According to this embodiment it is possible to design the thermistors differently to create thermistors of different thermal conductivity. This can be performed, for example, by the chosen thermistor material or by the composition of the material or alternatively by the structure of the material such as the crystallinity of the thermistor material. The inventors have found that a difference in thermal conductivity of both thermistors may provide the above described effect.

According to a further embodiment, the sensor system as described above may comprise a first interlayer and a second interlayer. The first interlayer is arranged in the heat conduction path between the first means for heating and the first thermistor in the first sensor. Analogously the second interlayer is arranged in the heat conduction path between the second means for heating and the second thermistor in the second sensor.

In the most general setup it is possible that the two interlayers are identical or similar concerning their thermal conductivity. In this case, for example, the difference in thermal conductivity of the heat conduction paths may be provided via the thermistor materials.

However, it is most preferred that the first interlayer has a higher thermal conductivity than the second interlayer. Form the point of increasing the difference in thermal conductivity it is most preferred that both the thermistors and the interlayers contribute to having different thermal conductivities in the heat conduction path of the first and the second sensor.

In an alternative embodiment the thermistors may be identical and the difference in thermal conductivity is provided via the interlayers. This may have advantages for constructing the sensor systems, as steering the thermal conductivity is achieved by designing the interlayers, while the measuring function which is provided the thermistors. This separation of functions may enable easier fabrication and allows for independent use of the thermistor material, which may be optimized independently for increased sensitivity.

According to another embodiment, the first interlayer and the second interlayer may comprise a chemically similar material or consist of such. Chemically similar material may mean that two oxide materials of the same metal. For example, the oxide may be silicon oxide. According to this embodiment, the first interlayer may have a higher degree of crystallinity or comprise crystallites with larger average size than the second interlayer. Also the second interlayer may be more amorphous than the first interlayer.

By having larger crystallites or a higher degree of crystallinity in general, the thermal conductivity can, for many or most materials, be improved significantly when compared to a highly disperse material of small crystallites or an amorphous material. In the case of silicon oxide as the material for the interlayers, the second interlayer may be amorphous or glass-like silicon oxide while the first interlayer may be polycrystalline silicon oxide with larger crystallites. Silicon oxide materials can be easily fabricated on silicon wafer substrates and are therefore advantageous for forming the interlayer.

Alternatively, or in addition to the previous, the thermal conductivity may also be adjusted by chemical means, such as doping.

According to another preferred embodiment the means for heating for both the first and the second interlayer may be an arrangement of one or several conductors wound to a meander-like form within a spatial plane. This means that a heating meander may be formed as the first and/or the second means for heating.

The sensor system may preferably comprise a power source for heating the first means for heating. Furthermore, it may comprise electronics which regulate the heating.

Furthermore, contacts and electronics for readout of the first and the second thermistor are also preferably provided in the sensor system.

According to another embodiment which has already been partly addressed above, the means for heating, also including a power supply for the first means for heating, and the second means for heating, together with a power supply for the second means for heating, are configured to provide different temperatures to the first thermistor and the second thermistor. This may mean that during operation of the sensor system, the first means for heating is capable of providing a different temperature to the first thermistor than the second means for heating is providing to the second thermistor.

For example, in a typical measurement configuration one of the first and the second thermistor functions as a measurement sensor and the other one as a reference sensor. For example, the second thermistor may be heated to a higher temperature than the first thermistor. In such a configuration the second sensor may act as the measurement sensor in which the second thermistor produces a higher change in thermistor temperature than the first upon a change in atmosphere composition. Accordingly the first sensor may provide an only slightly changed baseline, while the second sensor may provide a sensitive and intense measurement signal upon a change in gas composition.

According to another embodiment, it has been found by the inventors that preferably the first interlayer has a thermal conductivity of 5 W/(m·K) or higher and the second interlayer has a thermal conductivity of 1.4 W/(m·K) or below.

In this case the first interlayer, for example, is made of more crystalline silicon oxide material while the second interlayer may be made of amorphous or more polycrystalline silicon oxide material such as a thermal silicon oxide layer. The thermal silicon oxide layer roughly has a thermal conductivity of 1.4 W/(m·K).

Preferably, the difference in thermal conductivity is even larger. It is preferred that the second interlayer remains with the comparatively low thermal conductivity of 1.4 W/(m·K) or below, as thermal silicon oxide can be easily fabricated on a silicon wafer. However, it is preferred that, for example, by increasing the crystallinity of the first interlayer, a thermal conductivity of 10 W/(m·K) or above, of 20 W/(m·K) or above or of 50 W/(m·K) or above is provided. The inventors have found in particular for an embodiment with a first interlayer and a second interlayer that the higher the thermal conductivity of the first interlayer is, the more the sensitivity can be improved.

Furthermore, an alternative sensor system is provided, the features of which may or may not be combined with the above-mentioned features. This sensor system comprises a first sensor having a first thermistor for sensing a change in heat flow and a first means for heating the first thermistor. A first interlayer is arranged between the first thermistor and the first means for heating. A similar setup is present in the sensor system for the second sensor which has a second thermistor for sensing a change in heat flow and second means for heating the second thermistor and a second interlayer between the second thermistor and the second means for heating. In the second setup both the first and the second interlayer have a thermal conductivity of above 1.4 W/(m·K).

This embodiment may be even further generalized, as it is preferred that both interlayers have higher thermal conductivity than in state of the art sensors, such as in the above-mentioned US patent application US 2019/35607 A1. A thermal conductivity of 1.4 W/(m·K) or above, is an example in which the interlayer has a higher thermal conductivity than the technically conventional interlayers or insulation layers.

It is a long held belief in the field that both interlayers should be highly thermally insulating, i.e. to have low thermal conductivity, in order to enhance a temperature change in the thermistor layer, in order to improve sensitivity.

However, the inventors have found that state of the art thermistors allow for higher thermal conductivities without unacceptable deterioration of the sensitivity but with significant improvement of the response time of a thermistor.

The inventors have found that for example a steady state for a thermistor is reached faster if the thermal conductivity between the means for heating and the thermistor is high. This means that after a first change in measurement environment, such as a change in detectant concentration, a steady state is reached faster if the thermal conductivity of an interlayer is high. This means the sensor is capable of faster recognizing a second change and is capable of separating two changes following one after the other better than a sensor system with thermally isolative interlayers This alternative embodiment may be preferably combined with the other embodiment described above, as the difference in thermal conductivity between a heat conduction path in the first and second sensor provides additional sensitivity which may be used to at least partially compensate for a sensitivity loss upon an increase of thermal conductivity of both interlayers. Accordingly an embodiment is preferred in which the thermal conductivity of both interlayers is higher than 1.4 W/(m·K) and in addition the first interlayer has a higher thermal conductivity than the second interlayer.

It is preferred that the first and the second interlayer have a thermal conductivity of 2 W/(m·K) or more. Furthermore, it is even more preferred that they have a thermal conductivity of 5 W/(m·K) or more, of 10 W/(m·K) or more or even of 50 W/(m·K) or more. The higher the thermal conductivity, the higher the response time of the sensor system may be.

Furthermore, according to another embodiment, a sensor array comprising at least two of the above-described sensor systems is provided. In such an array the different sensor systems may be configured to detect different detectants. Accordingly, several of the sensor systems combined with electronics may allow for tracing several gases in a mixture, for example in a fingerprint-like manner optionally including comparison to a pre-recorded calibration database.

According to a further embodiment a process of using a sensor system according to the above-described embodiments is provided wherein the first and the second sensor are heated to different temperatures and wherein one of the sensors acts as a measurement sensor and the other one acts as a reference sensor. It is not limited whether the first or the second sensor is a reference or detecting sensor. This choice may depend on which type of gas is to be detected or, in more general terms, which type of change is to be recorded. It may depend on whether the recorded change rather increases heat flow from the sensor or whether it creates heat flow to the sensor or reduces the heat flow from the sensor.

In the process the sensor system becomes exposed to a gas atmosphere comprising a detectant and thereupon a difference in temperature change between the measurement sensor and the reference sensor is measured when compared to a steady state response of both sensors in a reference gas atmosphere without a detectant or a comparison of both sensor signals is indicative of the change in the gas atmosphere. Alternatively, the reference gas atmosphere may also comprise a detectant in a constant concentration and a change in the detecting concentration may be present which is for example an increase or a decrease.

As explained above, it is preferred in many cases, such as for the detection of $CO_2$, that the second sensor is the measurement sensor and the first sensor is the reference sensor. In this case it is preferred that the second sensor is heated to a higher temperature than the first sensor. For example, the first sensor may be heated to a temperature between 100° C. and 200° C. The second sensor may be heated to a temperature of above 200° C., such as a temperature between 250° C. and 350° C. For example, the first sensor may be heated to a temperature of 150° C. and the second sensor may be heated to a temperature of 300° C.

BRIEF DESCRIPTION OF THE DRAWINGS

In the following the invention is described in more detail with reference to schematic figures and experimental data. For the schematic figures it is noted that the components are not shown true to scale, but are only represented schematically. Accordingly, the components may be shown distorted in their size, lengths or length ratios. Accordingly, length or length ratios may not be taken from the schematic drawings.

DETAILED DESCRIPTION OF ILLUSTRATIVE EMBODIMENTS

Figure 1:
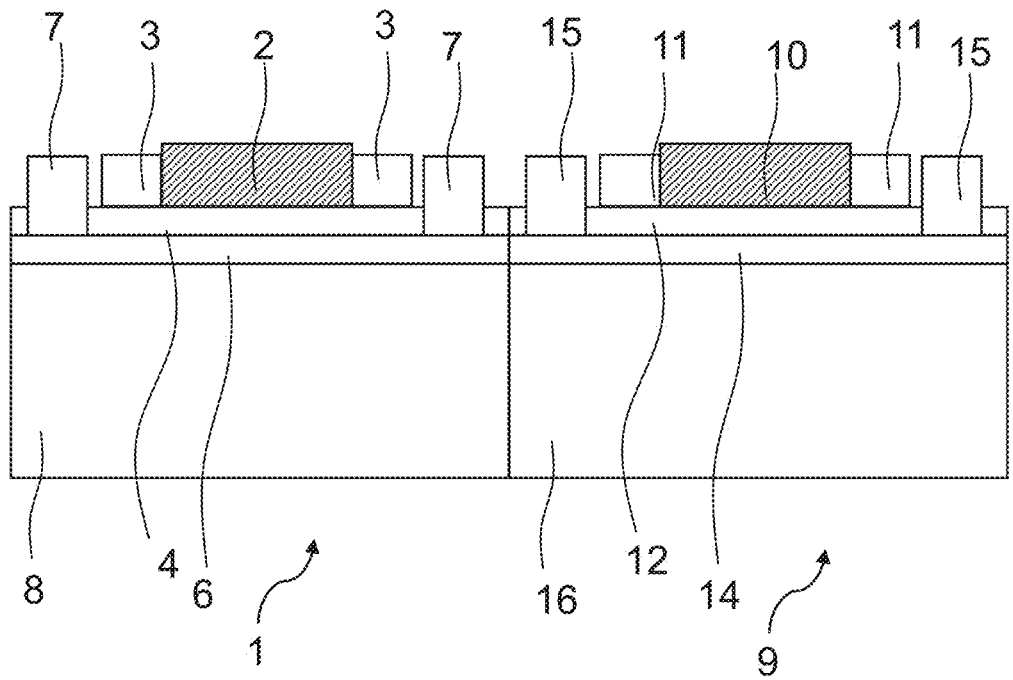
FIG. 1 shows a first embodiment of the present application in a schematic cross-section representation.

FIG. 1 shows a first representation of a sensor system 1. The sensor system 1 comprises two sensors, a first sensor 1 and a second sensor 9. The first sensor 1 comprises a first thermistor 2 which is connected to contacts 3 of the first thermistor 2 for read-out of the first sensor. Furthermore, the first sensor 1 comprises a first heating meander layer 6 as a first means for heating. The first heating meander layer 6 is provided on a first substrate 8. The first substrate 8 may comprise a further insulation layer arranged between the bulk material of the substrate and the heating meander layer 6 (not depicted). Furthermore, the first heating meander layer 6 comprises two external contacts 7 which allow the first heating meander layer 6 to be electrically contacted and to be supplied with power. In between the first heating meander layer 6 and the first thermistor 2 the first interlayer 4 is arranged.

The second sensor 9 comprises a second substrate 16 which is shown as a joint substrate with the first substrate 8. Alternatively, the substrates may also be separated substrates. Besides this, the setup of the second sensor 9 is similar to the first sensor 1. A second thermistor 10, which is electrically contacted by the contacts ii of the second thermistor 10, is arranged on top of a second interlayer 12. Below the second interlayer 12 a second heating meander layer 14 is provided as a second means for heating. The second heating meander layer 14 is arranged on the second substrate 16. The second heating meander layer 14 also comprises means for contacting (external contacts 15) in order to supply power to the second heating meander layer 14.

The substrates 8 or 16 may be any suitable substrate, for example a silicon substrate such as a silicon wafer.

The heating meander layers 6 are 14 are capable of providing heat to each thermistor 2 or 10. The heat is conducted from each of the heating meander layers 6 or 14 through each interlayer 4 or 12 to each thermistor 2 or 10, respectively. This can be identified as the heat conduction path in each sensor.

The thermistors 2 or 10 are NTC thermistor but, in variations of this embodiment, can be any suitable thermistor material such as a PTC thermistor.

he first interlayer 4 and the second interlayer 12 comprise silicon oxide as the main material, but variations of this embodiment may comprise any technically suitable material for an interlayer.

The first interlayer 4 has a higher thermal conductivity than the second interlayer 12. Thereby the heat conduction path between the first heating meander layer 6 to the first thermistor has a higher thermal conductivity than the other heat conduction path between the second heating meander layer 14 to the second thermistor 10. In particular, the second interlayer 12 may comprise polycrystalline silicon oxide material with finer crystallites than the first. Also the second interlayer 12 can comprise more amorphous silicon oxide material than the first interlayer 4. Accordingly, the first interlayer 4 preferably has a higher degree of crystallinity or on average larger crystallite sizes than the second interlayer 12. By these means the thermal conductivity of the first interlayer is higher than that of the second interlayer. For example, the thermal conductivity of the second interlayer 12 may be 1.4 W/(m·K) or smaller, while the first interlayer 4 has a thermal conductivity of above 1.4 W/(m·K). Most preferably the first interlayer has a thermal conductivity of 5 W/(m·K) or above.

In addition, optionally also the thermistor material of the first thermistor 2 may have a higher thermal conductivity than the thermistor material of the second thermistor 10 by which means the thermal conductivity may be further enhanced.

In an application it is preferred that the second sensor 9 is used as the measurement sensor, while the first sensor 1 is used as the reference sensor. If the thermal conductivity of the heat conduction path of the second sensor 9 is smaller than that of the first sensor 1, the second sensor 9 is more strongly affected by any change in the detection environment than the first sensor 1.

Figure 2:
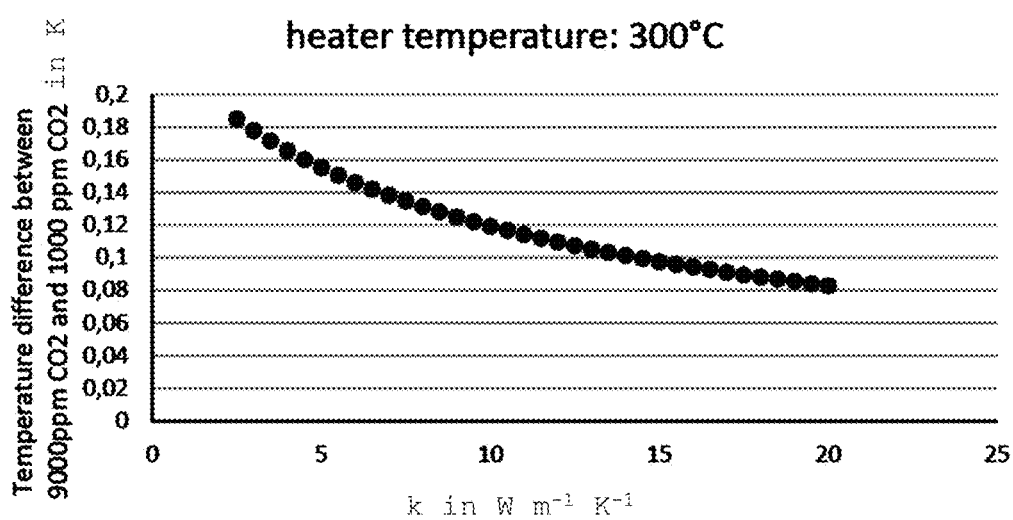
FIG. 2 shows computationally simulated data of the dependence of a temperature difference between different $CO_2$ gas concentrations in a test atmosphere in dependence on the thermal conductivity at 300° C. heating temperature.
Figure 3:
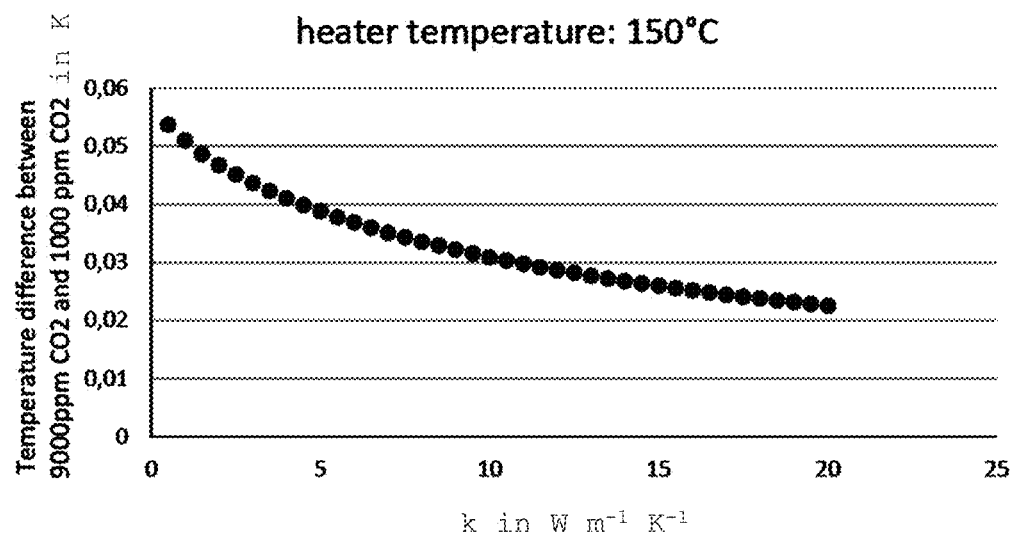
FIG. 3 shows computationally simulated data of the dependence of a temperature difference between different $CO_2$ gas concentrations in a test atmosphere in dependence on the thermal conductivity at 150° C. heating temperature.

FIGS. 2 and 3 show computed graphs for the temperature difference measured on a thermistor at two different atmospheric concentrations of $CO_2$, namely 9000 ppm and 1000 ppm $CO_2$, in dependence of the thermal conductivity of an insulation layer. FIG. 2 addresses an elevated temperature of 300 K, which is advantageously applied as the temperature at which the measurement sensor is operated. In FIG. 3 the graph is shown for the temperature of 150° C., which is an advantageous temperature for a reference sensor to be operated.

In both cases the individual graphs show that at low thermal conductivity of below 5 W/(m·K) the difference in temperature of the thermistor is highest, while at the maximum computed thermal conductivity of 20 W/(m·K) the temperature difference is lowest.

In a state of the art sensor system, the same thermal conductivity, would be chosen for both interlayers. If it is assumed that in such a case both interlayers have the same thermal conductivity of 5 W/(m·K), a difference in response between the two sensors operated at 300 and 150° C. of roughly 0.1 K apparent, if FIGS. 2 and 3 are compared.

However, this difference can be further enhanced if the measurement sensor heated to 300° C. has a low thermal conductivity such as below 5 W/(m·K) or even lower, for example as low as 1.5 W/(m·K), while the reference sensor that is heated to 150° C. has a high thermal conductivity, for example above 5 W/(m·K), 10 W/(m·K), 15 W/(m·K) or 20 W/(m·K). The exact differences in thermal conductivity can be directly obtained by comparing the two curves of FIGS. 2 and 3. However, as can also be seen from the graphs, the slightest difference in thermal conductivity may already produce a gradual enhancement of the difference between measurement sensor and reference sensor. For example, if the measurement sensor (second sensor) is operated at 300° C. and the thermal conductivity of the second interlayer is in the range of 3 W/(m·K), while the reference sensor (first sensor) is operated at 150° C. and the thermal conductivity of the first interlayer is 20 W/(m·K), a difference in detected temperature difference of nearly 0.16 K between both sensors can be obtained. Accordingly, a measurement signal can be enhanced by about 40%, compared to the above comparison.

Figure 4:
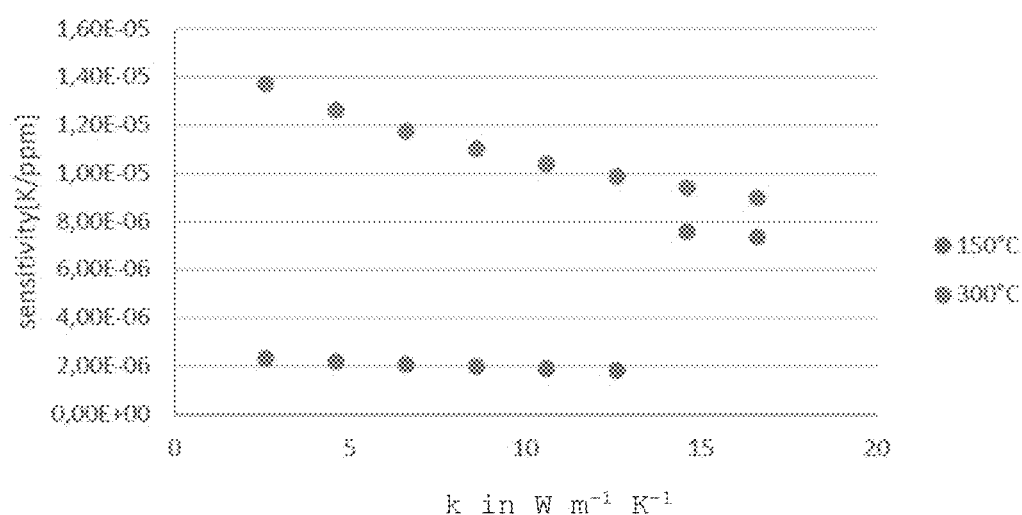
FIG. 4 shows the computationally simulated data of the sensitivity of $CO_2$ gas detection for thermistors heated to different temperatures in dependence on the thermal conductivity.

In FIG. 4 a similar depiction is shown for the simulation of the thermal conductivity of the thermistor material for a sensor at 150° C. (lower eight dots) against the thermal conductivity at 300° C. (higher eight dots). It is shown that the sensitivity measured in K/ppm of the detected gas ($CO_2$), decreases for the measurement sensor (operated at 300° C.) with increasing thermal conductivity of the thermistor material. However, at 150° C. the sensitivity remains mainly the same up to around 12.5 W/(m·K), but at 15 W/(m·K) a jump in sensitivity for the reference sensor operated at 150° C. is observed. Accordingly, it is again proven that it is advantageous to have a low thermal conductivity for the second thermistor material but to have a high thermal conductivity for the first thermistor material.

It is advantageous to combine the results as described for FIGS. 2 and 3 and for FIG. 4.

In an alternative embodiment which is not depicted separately, but which may have the same layer stacking as described for FIG. 1, both the first interlayer 4 and the second interlayer 12 have comparatively high thermal conductivity of higher than 1.5 W/(m·K), such as 2 W/(m·K) or more preferably 5 W/(m·K) or higher. The inventors found that if the thermal conductivity is high, the response time of the sensor is increased. In particular, a steady state is reached much faster in the case that thermal conductivity is high. Accordingly, the sensor can detect additional change in gas composition much faster.

If the thermistor is sensitive enough, it is possible that both interlayers have the same high thermal conductivity. However, as described above, the presence of different thermal conductivities is preferred, which allows to partly compensate for a sensitivity loss due to overall increased thermal conductivity for both sensors.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A sensor system comprising:
   a first sensor having a first thermistor configured to sense a change in heat flow and a first heater configured to heat the first thermistor; and
   a second sensor having a second thermistor configured to sense a change in heat flow and a second heater configured to heat the second thermistor,
   wherein a heat conduction path between the first heater and the first thermistor has a higher thermal conductivity than a heat conduction path between the second heater and the second thermistor, and
   wherein the heat conduction path in the first sensor is a path along which the heat is conductable between the first heater and the first thermistor, and the heat conduction path in the second sensor is a path along which the heat is conductable between the second heater and the second thermistor.

2. The sensor system according to claim 1, wherein the heat conduction path between the first heater and the first thermistor includes the first thermistor itself and the heat conduction path between the second heater and the second thermistor includes the second thermistor itself, and wherein the first thermistor has a higher thermal conductivity than the second thermistor.

3. The sensor system according to claim 1, wherein the heat conduction path between the first heater and the first thermistor includes a first interlayer arranged between the first heater and the first thermistor, and wherein the heat conduction path between the second heater and the second thermistor includes a second interlayer arranged between the second heater and the second thermistor.

4. The sensor system according to claim 3, wherein the first interlayer has a higher thermal conductivity than the second interlayer.

5. The sensor system according to claim 3, wherein the first interlayer and the second interlayer comprise a chemically similar material, and wherein the first interlayer has a higher degree of crystallinity and/or comprises crystallites with a larger average size than the second interlayer.

6. The sensor system according to claim 3, wherein the first and second interlayers comprise a silicon oxide material.

7. The sensor system according to claim 3, wherein the first interlayer has a thermal conductivity of 5 W/(m·K) or above and the second interlayer has a thermal conductivity of 1.4 W/(m·K) or below.

8. The sensor system according to claim 1, wherein each of the first and second heaters is an arrangement of one or several conductors wound to a meander-like form within a spatial plane.

9. The sensor system according to claim 1, wherein, under constant conditions or steady state conditions, the first heater together with a power supply for the first heater and the second heater together with a power supply for the second heater are configured to provide different temperatures to the first thermistor and the second thermistor.

10. A sensor array comprising:
at least two sensor systems according to claim 1, which are configured to detect different detectants.

11. A method for using the sensor system according to claim 1, the method comprising:
heating the first sensor and the second sensor to different temperatures, wherein one of the sensors acts as a measurement sensor and the other sensor acts as a reference sensor; and
exposing the sensor system to a gas atmosphere comprising a detectant; and
measuring a difference in temperature change between the measurement sensor and the reference sensor when compared to a steady state response of both sensors in a reference gas atmosphere without the detectant.

12. A sensor system comprising:
a first sensor having a first thermistor configured to sense a change in heat flow and a first heater configured to heat the first thermistor; and
a second sensor having a second thermistor configured to sense a change in heat flow and a second heater configured to heat the second thermistor,
wherein a heat conduction path between the first heater and the first thermistor has a higher thermal conductivity than a heat conduction path between the second heater and the second thermistor,
wherein the heat conduction path between the first heater and the first thermistor includes a first interlayer arranged between the first heater and the first thermistor,
wherein the heat conduction path between the second heater and the second thermistor includes a second interlayer arranged between the second heater and the second thermistor, and
wherein the first interlayer has a higher thermal conductivity than the second interlayer.

13. The sensor system according to claim 12, wherein the first and second interlayers comprise a silicon oxide material.

14. The sensor system according to claim 12, wherein the first interlayer has a thermal conductivity of 5 W/(m·K) or above and the second interlayer has a thermal conductivity of 1.4 W/(m·K) or below.

15. The sensor system according to claim 12, wherein each of the first and second heaters is an arrangement of one or several conductors wound to a meander-like form within a spatial plane.

16. The sensor system according to claim 12, wherein, under constant conditions or steady state conditions, the first heater together with a power supply for the first heater and the second heater together with a power supply for the second heater are configured to provide different temperatures to the first thermistor and the second thermistor.

17. A sensor system comprising:
a first sensor having a first thermistor configured to sense a change in heat flow and a first heater configured to heat the first thermistor; and
a second sensor having a second thermistor configured to sense a change in heat flow and a second heater configured to heat the second thermistor,
wherein a heat conduction path between the first heater and the first thermistor has a higher thermal conductivity than a heat conduction path between the second heater and the second thermistor,
wherein the heat conduction path between the first heater and the first thermistor includes a first interlayer arranged between the first heater and the first thermistor,
wherein the heat conduction path between the second heater and the second thermistor includes a second interlayer arranged between the second heater and the second thermistor,
wherein the first interlayer and the second interlayer comprise a chemically similar material, and
wherein the first interlayer has a higher degree of crystallinity and/or comprises crystallites with a larger average size than the second interlayer.

18. The sensor system according to claim 17, wherein the first and second interlayers comprise a silicon oxide material.

19. The sensor system according to claim 17, wherein the first interlayer has a thermal conductivity of 5 W/(m·K) or above and the second interlayer has a thermal conductivity of 1.4 W/(m·K) or below.

20. The sensor system according to claim 17, wherein each of the first and second heaters is an arrangement of one or several conductors wound to a meander-like form within a spatial plane.

* * * * *